United States Patent [19]

Arnold et al.

[11] Patent Number: 5,491,240
[45] Date of Patent: Feb. 13, 1996

[54] QUATERNARY COMPOUND OF A TERTIARY AMINE AND METHYL CHLORIDE

[75] Inventors: Timothy C. Arnold, Janesville, Wis.; Robert E. Mehaffey, Jr., Easley, S.C.

[73] Assignee: Witco Corporation, Greenwich, Conn.

[21] Appl. No.: 315,104

[22] Filed: Sep. 29, 1994

[51] Int. Cl.$^6$ .................... C07D 233/14; C07D 233/24; C07C 85/04; C07C 87/30
[52] U.S. Cl. ........................................ 548/347.1; 564/296
[58] Field of Search ........................ 548/347.1; 564/296

[56] References Cited

U.S. PATENT DOCUMENTS

| 2,493,321 | 1/1950 | Shonle et al. | 548/347.1 |
| 3,175,008 | 3/1965 | Shapiro et al. | 564/296 |
| 3,557,214 | 1/1971 | Koenig et al. | 564/296 |
| 3,965,178 | 6/1976 | Johnson et al. | 564/296 |
| 4,233,451 | 11/1980 | Pracht et al. | 548/354 |

FOREIGN PATENT DOCUMENTS

| 0294219 | 9/1969 | Australia | 564/296 |
| 0288857 | 11/1988 | European Pat. Off. | 564/296 |
| 58-67649 | 4/1983 | Japan | 564/296 |
| 60-56940 | 4/1985 | Japan | 564/296 |
| 0678865 | 10/1975 | U.S.S.R. | 564/296 |

*Primary Examiner*—Floyd D. Higel
*Attorney, Agent, or Firm*—Scully, Scott, Murphy & Presser

[57] ABSTRACT

Disclosed is a process for producing quaternary ammonium compounds wherein a reaction mixtures containing only the corresponding unquaternized amine compound and the quaternizing agent are reacted together under conditions such that no unreacted quaternizing agent remains in the fully quaternized product. The reaction is carried out initially free of solvents. Minimal amounts of solvent that may be introduced near the end of the quaternization to maintain adequate fluidity of the reaction mixture.

7 Claims, No Drawings

QUATERNARY COMPOUND OF A TERTIARY AMINE AND METHYL CHLORIDE

BACKGROUND OF THE INVENTION

The present invention relates to the production of quaternary ammonium compounds.

Quaternary ammonium compounds are useful as fabric softeners and/or as conditioning agents for the skin or hair. Quaternary ammonium compounds are also useful in other applications, such as softening and debonding of paper products, in the production of fiberglass, car wash performance products, and phase transfer catalysts.

Thus, the present invention relates more particularly to the production of quaternary ammonium compounds wherein the desired quaternary ammonium product is manufactured as a product which can readily be formulated into compositions having these or any other uses and which provide the desired quaternary ammonium compound free of undesirable auxiliary and side products and side reactions.

Quaternary ammonium compounds of the type described herein are frequently synthesized by reacting a corresponding tertiary amine with a quaternizing compound. A portion of the quaternizing compound bonds preferentially to the nitrogen of the tertiary amine, thereby producing the desired quaternary ammonium compound as a cation whose charge is balanced by the anion remaining from the quaternizing agent. The quaternizing reaction is typically carried out in a solvent in which the tertiary amine and quaternizing agent reactants are soluble. The use of such a solvent is considered desirable in order to achieve maximal contact between the reactants and in order to attain and retain fluidity of the reaction mixture at the relatively elevated temperatures at which the quaternization reaction is customarily carried out.

However, the conventional reaction conditions employed when reacting the tertiary amine and quaternizing agent in a solvent lead to conditions during and following the reaction which conditions, while relatively undesirable, have come to be tolerated because they are believed to be outweighed by the benefits of obtaining the desired quaternized product in the yields that can be obtained. Simply put, however, these drawbacks are also considered to be relatively unavoidable in the interest of obtaining the desired quaternized product without resort to conditions and/or reactants which are so expensive or difficult to manage as to render the quaternizing process excessively expensive and inefficient.

For instance, reaction in solvent can lead to formation of a reaction product containing two and sometimes three distinct liquid phases. This result, while it can be dealt with using conventional processing technology, is still to be considered relatively undesirable, because separating the various phases imposes additional processing steps and requires additional equipment. Furthermore, to the extent that the desired product reports to more than one of such phases, recovering the phases separately, as must be done, leads to a sacrifice in the overall yield of the desired quaternary product unless each phase is to be treated separately following separation in order to recover the quaternary product.

In addition, the reaction product is often characterized by being off-color and/or off-odor. This characteristic is believed to be inherent in the reactivities of the tertiary amine and the quaternizing agent, in that the reaction conditions employed to cause the tertiary amine to react with the quaternizing agent are believed to lead inevitably to a certain amount of formation of, for instance, products formed by reaction of the tertiary amine with itself, or with the quaternized product (such as disproportionation reactions) thereby producing a variety of nitrogen-containing end products in addition to the desired quaternary ammonium product. It can be appreciated that separation of the byproducts, which are after all impurities, from the desired quaternary ammonium product is particularly difficult given the similar chemical natures of the byproduct and the desired end product. This problem of reactivities is compounded whenever the solvent chosen has any tendency to engage in competitive reactions or to promote the occurrence of competitive side reactions. Thus, the conventional technology of quaternizing reactions requires a careful selection of the proper solvents to minimize the contribution of the solvent system to the tendency of the amine to undergo competitive side reactions.

Accordingly, there remains a need in this area of technology for a process for forming desired quaternary ammonium compounds while suffering at most a minimal tendency for the reactants to engage in competitive side reactions. This need is emphasized by the fact that formulators of end products such as fabric softeners, hair conditioners, and skin conditioners, prefer to obtain the quaternary ammonium ingredients essentially in the form, and in particular, in association with the solvent system, in which the quaternary ammonium compounds have been synthesized. This feature permits the formulators to avoid having to recover the quaternary ammonium compound from one solvent system and then to reincorporate it into another solvent system or into the final composition for use by the consumer. This fact, however, severely restricts the choice of solvent systems available to the manufacturer of the quaternary ammonium compound. Thus, there remains a particular need for a process for forming quaternary ammonium compounds useful in applications such as fabric softeners, hair conditioners, and skin conditioners, which produces such quaternary ammonium compounds in a solvent system compatible with the intended end use of the quaternary ammonium compound.

BRIEF SUMMARY OF TEE INVENTION

The present invention satisfies these objectives while avoiding the undesirable drawbacks which characterize prior attempts to resolve the problems described herein.

One aspect of the present invention resides in a process for forming a quaternary ammonium compound, comprising (a) providing in a reaction vessel a molten product which is a tertiary amine of the formula (1a)

$(R^1)N(R^2)(R^3)$            (1a)

or an imidazoline of the formula (1b)

$CH_2-N=C(R^3)-N(R^2)CH_2$            (1b)

wherein either of the adjacent pair of carbon atoms can be substituted with $R^4$, wherein $R^1$ is a lower alkyl group containing 1 to 6 carbon atoms, and $R^2$, $R^3$ and $R^4$ are the same or different and each has the formula $R^a$—O—$(CH_2)_b$— or $R^a$—, wherein $R^a$ is a straight or branched alkyl or alkylene radical containing 12 to 24 carbon atoms and 0 to 3 carbon-carbon double bonds, and b is 1 to 4, which molten product is free of solvent;

(b) establishing a reduced pressure in said reaction vessel over said molten product, which is effective to purge said product of gases;

(c) completely quaternizing said molten product by reacting it with a quaternizing agent consisting of one or more compounds of the formula QX, wherein Q is hydrogen, benzyl, methyl or ethyl and X is a monovalent anion, capable of quaternizing said product under quaternizing conditions, under conditions such that the product formed by said reaction contains no unreacted quaternizing compounds, the combination of said product and quaternizing agent constituting a reaction mixture;

(d) adding solvent to said reaction mixture only if necessary to maintain said reaction mixture in a fluid state before the completion of said quaternization and then not before the viscosity of the reaction mixture is within 10% of no longer being fluid, and only in an amount sufficient to fluidize said reaction mixture and solubilize unreacted quaternizing agent but insufficient to cause a second phase to form in said reaction mixture; and (e) recovering a product comprising high-purity quaternary ammonium compound of the formula (2a)

$$(R^1)(Q)\overset{+}{N}(R^2)(R^3) \cdot X^- \tag{2a}$$

or the formula (2b)

$$\overline{CH_2-N=C(R^3)-N(Q)(R^2)CH_2} \tag{2b}$$

wherein Q, $R^1$, $R^2$ and $R^3$ are as defined above and either of the adjacent pair of carbon atoms in formula (2b) can be substituted with $R^4$ as defined above from said reaction vessel.

DETAILED DESCRIPTION OF THE INVENTION

The quaternary ammonium compounds that can be produced to advantage by the process of the present invention correspond to the following formula (2a)

$$(R^1)(Q)\overset{+}{N}(R^2)(R^3) \cdot X^- \tag{2a}$$

or the following formula (2b)

$$\overline{CH_2-N=C(R^3)-N(Q)(R^2)CH_2} \tag{2b}$$

wherein either of the two adjacent carbon atoms can be substituted with $R^4$, wherein Q represents hydrogen or a methyl, ethyl or benzyl group and preferably represents methyl or ethyl;

$R^1$ is a lower alkyl group containing 1 to 6 carbon atoms, and is preferably methyl, ethyl, or propyl; and $R^2$, $R^3$ and $R^4$ are the same or different and each represents substituents of the formula $R^a$— or $R^a$—O—$(CH_2)_b$—, wherein $R^a$ is a straight or branched alkyl or alkylene radical containing 12 to 24 carbon atoms and 0, 1, 2 or 3 carbon-carbon double bonds, and b is 1 to 4. It should be noted that the products that can be produced within the scope of the present invention include mixtures of two or more compounds each corresponding to formula (2). Such mixtures are frequently formed when the source material is derived from naturally occurring sources, wherein the tertiary amine or the reactants employed in forming the tertiary amine present a variety of chain lengths $R^a$.

The anion $X^-$ is any organic or inorganic anion consistent with the reaction processes described herein and consistent with the desired properties of the final quaternary ammonium product. Examples of suitable anions include halides such as chloride, bromide and iodide, methyl sulfate, ethyl sulfate, $H_2PO_4^-$ and acetate. Thus, suitable quaternizing compounds include dimethyl sulfate, diethyl sulfate, benzyl chloride, methyl chloride, methyl bromide, glacial acetic acid, and phosphoric acid.

The process of the present invention preferably begins with an amine which is a tertiary amine which is an acyclic compound of the formula (1a)

$$(R^1)N(R^2)(R^3) \tag{1a}$$

wherein $R^1$, $R^2$ and $R^3$ have the definitions set forth hereinabove, or an imidazoline of the formula (1b)

$$\overline{CH_2-N=C(R^3)-N(R^2)CH_2} \tag{1b}$$

wherein either of the carbon atoms forming an adjacent pair can be substituted with a group $R^4$ whose definition is the same as that of $R^2$ and $R^3$.

The tertiary amine or imidazoline, or a mixture of tertiary amines corresponding to formula (1a), is placed into a reaction vessel of the type capable of heating and stirring the charge within the vessel, capable of maintaining a vacuum in the head space above the charge, and capable of feeding reagents and solvents into the interior of the vessel while maintaining any desired pressure and temperature therein.

The tertiary amine or imidazoline is placed in the interior of the reactor vessel, and the vessel is then closed. Heat is applied to the product to melt it, and a vacuum is established over the melting product. The temperature should be maintained about 50°–100° F. above the melting point of the tertiary amine or imidazoline to ensure that it remains molten during the addition of reagents which are subsequently added. The temperature is generally about 180° F. to about 240° F., more preferably about 190° F. to about 220° F. Higher temperatures can be employed but are not necessary and may prove to be deleterious to the quality of the product. The vacuum that is established over the product should be sufficient to purge the molten product of gaseous components dissolved or dispersed therein, such as oxygen and airborne impurities. Pressure on the order of about 80 to about 100 mmHg, or less, is generally sufficient to provide the desired degree of vacuum.

At this point, no solvent is present in the reaction vessel. By "solvent" is meant any material in which the tertiary amine or imidazoline or its quaternized product is soluble. Examples include water, alkanes, alkenes, alcohols, polyethylene glycols, polypropylene glycols, and mixtures thereof, and the like. Such solvents would generally have molecular weights of about 100 to 1000. The amine charged to the reaction vessel may at this point comprise more than one amine of the formulas (1a) and/or (1b) as described above. Preferably, the charge consists entirely and solely of the amine(s). This charge may also contain inert, non-reactive and non-volatile components which will not enter into competitive reactions during or following the quaternization step. If the charge contains volatilizable components, especially water, oxygen, and solvents, these should be removed and the establishment of vacuum over the tertiary amine is intended to remove such volatilizable components.

In particular, the charge is kept free of products that would enter into competitive reactions with the compounds of formulas (1a) and (1b) such as transesterification reactions.

Tests have shown that customary solvents such as propylene glycol can react with amines of formula (1a) and (1b) even though they would not react with the products of formulas (2a) and (2b).

Next, the quaternizing agent is introduced into the reaction vessel and reacted with the amine. The quaternizing agent as introduced is free of any material which may act as a solvent for the quaternizing agent, for the amine, or for the desired quaternary ammonium product. Preferably, the quaternizing agent consists solely of one or more compounds capable of quaternizing the amine(s) present under quaternizing conditions.

The quaternizing agent can be introduced all at once or can be metered in gradually during the course of the quaternizing reaction. Preferably, the amine is kept molten, and the fluid reaction mixture of amine and quaternizing agent is agitated sufficiently to provide intimate contact throughout the reaction vessel between the amine and the quaternizing agent.

The total amount of quaternizing agent added should be sufficient to ensure completion of the reaction; and will generally exceed the amount stoichiometrically equivalent to the amount of quaternizable amine present. Methyl chloride, for instance, quaternizes the amine, and any unreacted excess volatilizes off and out of the vessel. There preferably should be no unreacted quaternizing agent present in the molten amine phase when the quaternization has been completed.

As the reaction proceeds, the reaction mixture tends to increase in viscosity as the amount of quaternary ammonium compound increases relative to the amounts of amine and quaternizing agent which are present. Increased viscosity will, of course, cause agitation of the reaction mixture to become more difficult and eventually fruitless. This situation can be remedied by raising the temperature of the reaction mixture somewhat, but raising the temperature is generally not a completely satisfactory resolution because higher temperatures risk causing side reactions and degradation of the desired quaternary ammonium product. Accordingly, near the end of the reaction, a small amount of solvent for the reaction mixture can be introduced into the reaction vessel. The solvent is added at or after the point at which the viscosity of the reaction mixture is within 10%, or even 5%, of the viscosity at which the reaction mixture is no longer fluid at the temperature at which the quaternization is being carried out. By "fluid" is meant that the reaction mixture is a continuous liquid which can be poured from the reaction vessel. In this way, the reaction mixture does not become too viscous to be stirred. Waiting too long has the disadvantage that additional efforts need to be expended to disperse the solvent into the hardening reaction mixture. Generally, the solvent is added when the reaction has proceeded past 50% conversion of the amine to quaternary ammonium compound, and generally past conversion of 85% and preferably past conversion of 90% of the amine. Preferably, no solvent is added before the free amine value of the reaction mixture has reached below 10% and more preferably below 5%.

Unlike conventional quaternization techniques, in this aspect of the present invention, care must be exercised in the choice of the solvent and in the choice of the amount thereof to introduce into the reaction vessel. Preferably, the solvent is introduced only at or after the point at which the viscosity of the reaction mixture has begun to increase. Thus, it should be recognized that in some embodiments of this invention it will not be necessary to add solvent at all until after the quaternization is complete.

The amount of solvent that is added should help to fluidize the reaction mixture, by which is meant that it makes the reaction mixture sufficiently fluid that it can be stirred. The amount of solvent that is added should also be sufficient to solubilize some, or all, unreacted quaternizing agents present in the reaction vessel, to help effectuate completion of any as yet uncompleted quaternization. However, the amount of solvent added must be limited to an amount insufficient to form a second phase in the reaction vessel. That is, the reaction mixture of amine and quaternizing agent form a one-phase composition in the reaction vessel, and any solvent subsequently added thereto must permit the reaction mixture in combination with the solvent to remain a one-phase composition. This requirement is met by using a sufficiently small amount of solvent, typically on the order of about 40 wt. % (based on the amount of amine and quaternizing agent present), and more preferably less than about 30 wt. % thereof. These percentages are illustrative; they will vary somewhat with the identity of the amine(s) and the quaternizing agent(s).

Preferred solvents that can be used in the present invention include lower alkanols, glycols and polyglycols. Preferred alkanols include those containing 1 to 6 carbon atoms, more preferably including ethanol, n-propanol, isopropanol, and butanols. Preferred glycols and polyglycols include ethylene glycol, 1,2-propanediol, 1,3-propanediol, propylene glycol, and polyethylene glycols and polypropylene glycols having molecular weights up to about 400–500. The solvent should be capable of forming a monophasic composition with the molten quaternary ammonium compound and any remaining unreacted tertiary amine and quaternizing agent.

The quaternization reaction is preferably allowed to proceed to completion, which helps simplify the recovery of the desired quaternary ammonium product from the reaction mixture and avoids risk of side reactions. Thus, in general, it is preferred to employ no more than a stoichiometric equivalent of quaternizing agent. The degree of conversion of the amine to the quaternary ammonium compound can be determined in conventional manner, for instance by periodically monitoring the amine content of the reaction mixture.

When the quaternization reaction has proceeded to the desired degree, the reaction is discontinued, typically by removing the heat source and venting the reaction vessel to a suitable recovery system or chamber. Then, any volatile unreacted quaternizing agent can be simply removed from the reaction mixture by vacuum (as noted above, excess amounts of non-volatile quaternizing compounds are not employed).

The product thus obtained is one or more quaternary ammonium compounds of the formula (2) set forth hereinabove. It has been determined that forming this quaternary ammonium product in this manner provides the product in a form which is immediately useful in compounding of compositions useful as fabric softeners, hair conditioning products, skin conditioning products, paper manufacturing agents, fiberglass production agents, car wash products, and the like. The product obtained in this manner is notably free of second and/or third phases and does not exhibit any undesirable off-color or undesirable odor. The product thus obtained is also stable in the sense that it does not take on off-color or undesirable odor subsequent to its recovery, whereas some quaternary ammonium compounds produced by conventional means do exhibit such a tendency. In addition, no quaternary ammonium product is lost to a second or third product phase, and steps heretofore believed to be necessary in conventional processing technology for recovery of such product from such phases are not necessary in carrying out the process of the present invention.

The following examples will illustrate the procedure employed in the process of the present invention.

EXAMPLE 1

One mole (595 grams) of tertiary amine was charged to a 5 gallon reactor. The reactor was sealed, and the charge was purged with nitrogen to 10 psig under vacuum. Further vacuum was drawn to 20–25 inches of mercury and purged to 10 psig two times. The charge was then heated to 210° F., evacuated to 25 inches of mercury, and then 820 grams of methylchloride was added at 58 psig. About 40 minutes later another 80 grams of methylchloride was added to a pressure of 62 psig. Four hours later the pressure was 14 psig, and the amine content of the reactor was determined to be 12.7. Another two hours later, the reaction mixture has a free-amine value of 6.8, and was observed to be thick and foamy. About 5,500 grams of polyethylene glycol (PEG-400) was added at this point, and 6 psig of methylchloride was vented off. Another 80 grams of methylchloride was added under nitrogen to raise the pressure to 10 psig. Another 2.2 hours later, the system pressure was 3 psig, and the free-amine value was 2.7. Another 20 grams of methyl chloride was added to bring the free-amine value closer to 2. Nitrogen was added to a system pressure of 12 psig. One hour later, the reactor contents were vented to 0 psig. Stirring was continued with a slight nitrogen sparge for another 10 minutes, and methylchloride was then stripped off under vacuum. The resulting reaction product had a satisfactorily high quaternary amine value, a clear color, and a free-amine value of about 2.0, and a final methylchloride content of about 361 ppm.

EXAMPLE 2

About 1,800 grams of a tertiary amine from naturally occurring sources, comprising amines substituted with alkyl chains having a variety of chain lengths, was charged to a reactor, and was then purged at a pressure of 20–25 inches of mercury under nitrogen to a final pressure of 10 psig. The reactor contents were heated to about 220° F. and evacuated to 25 inches of mercury. At this point addition of methylchloride began. Methylchloride was added stagewise over the next three hours. The free-amine value was sampled during this time and thereafter, and when the free-amine value had reached about 12 at about four hours after the initial addition of the methylchloride, the product was observed to be thick and foaming. Then about 400 grams of PEG-400 was added, and the pressure was adjusted to about 45 psig. The contents were stirred all this time. About another hour later the free-amine value was 4.1, and two and a half hours after this point the free-amine value had dropped to 2.6 whereupon the reactor contents were vented to strip off the methylchloride. Thereafter, another 358 grams of PEG-400 was added with stirring for about 20 minutes to assist the further stripping of methylchloride to a final value of about 148 ppm. About three hours later, another 816 grams of PEG-400 was added, and the contents were heated to 190° F. with stirring. The next morning the product was observed to be a single phase product. It contained about 48.76% of quaternary ammonium product and had a satisfactorily clear color.

EXAMPLE 3

One mole of imidazoline was charged to a pressure reactor. The temperature was raised to 220° F. at a vacuum of about 20 inches of mercury, and addition of methylchloride was begun. Addition of methylchloride continued over the next hour during which the free-amine value was observed to decline steadily to about 1.2. The reaction mixture was continually sparged with nitrogen, maintaining a pressure of about 10 psig. The reaction mixture was observed through the foaming. About an hour after the introduction of methylchloride began, 100 grams of propylene glycol was stirred into the reaction mixture, and stirring was continued for the next half hour. The reactor contents were then vented, but were kept heated to assist in venting off excess methylchloride. The product contained about 88.97 grams of quaternized imidazoline in propylene glycol with a free-amine value of 0.67.

EXAMPLE 4

In a comparative example, attempts were made to produce dimethyl diester quaternary ammonium compound by a conventional procedure, and by the procedure of this invention.

Using a conventional procedure, methyl diester amine was mixed with a solvent, polyethylene glycol ("PEG 400"). The mixture was heated and pressurized with methyl chloride. Analysis of the product showed that it was a mixture of amine and quaternary products in the PEG-400, corresponding to a yield of 50%.

Using the procedure of the present invention, methyl diester amine was reacted with methyl chloride in the absence of solvent. The reaction proceeded quickly; near the end, a small amount of PEG-400 was added to maintain fluidity of the reaction mixture. Analysis of the product showed dimethyl diester quaternary ammonium chloride, PEG-400, and a small amount of dimethyl monoester ammonium chloride. There were no side products, including no transesterification products at a detection limit of 5 mole % vs the diester quaternary product. Analysis of portions stored at 160° F. for 7 and 14 days showed no changes in the product.

What is claimed is:

1. A process for forming a quaternary ammonium compound, comprising (a) placing in a reaction vessel a molten amine which is a tertiary amine of the formula (1a)

$(R^1)N(R^2)(R^3)$ (1a)

or an imidazoline of the formula (1b)

$\overline{CH_2-N=C(R^3)-N(R^2)CH_2}$ (1b)

wherein either of the adjacent pair of carbon atoms is unsubstituted or is substituted with $R^4$, wherein $R^1$ is a lower alkyl group containing 1 to 6 carbon atoms, and $R^2$, $R^3$ and $R^4$ are the same or different and each has the formula $R^a$—O—$(CH_2)_b$— or $R^a$—, wherein $R^a$ is a straight or branched alkyl or alkylene radical containing 12 to 24 carbon atoms and 0 to 3 carbon-carbon double bonds, and b is 1 to 4, which molten amine is free of solvent;

b) reducing pressure within said reaction vessel so that a vacuum is established over said molten amine, which is effective to purge said amine of gases;

(c) completely quaternizing said molten amine by reacting it with a quaternizing agent consisting of one or more compounds of the formula QX, wherein Q is hydrogen, benzyl, methyl or ethyl and X is a monovalent anion, capable of quaternizing said amine such that the product formed by said reaction contains no unreacted quaternizing compounds, the combination of amine and quaternizing agent constituting a reaction mixture;

(d) adding solvent to said reaction mixture only if necessary to maintain said reaction mixture in a fluid state before the completion of said quaternization and then not before the viscosity of the reaction mixture is within 10% of no longer being fluid, and only in an amount sufficient to fluidize said reaction mixture and solubilize unreacted quaternizing agent but insufficient to cause a second phase to form in said reaction mixture; and (e) recovering a product comprising high-purity quaternary ammonium compound of the formula (2a)

$$(R^1)(Q)\overset{+}{N}(R^2)(R^3).X^- \qquad (2a)$$

or the formula (2b)

$$\overline{CH_2-N=C(R^3)-\overset{+}{N}(Q)(R^2)CH_2}.X^- \qquad (2b)$$

wherein Q, $R^1$, $R^2$ and $R^3$ are as defined above and either of the adjacent pair of carbon atoms in formula (2b) is unsubstituted or is substituted with $R^4$ as defined above from said reaction vessel.

2. The process of claim 1 wherein said molten tertiary amine has the formula (1a) and the quaternary ammonium compound which is recovered as the formula (2a).

3. The process of claim 1 wherein an imidazoline of formula (1b) is provided in step (a), and step (e) comprises recovering a quaternary ammonium compound of the formula (2b).

4. The process of claim 2 wherein the solvent is selected from the group consisting of lower alkanols, glycols and polyglycols and mixtures thereof.

5. The process of claim 3 wherein the solvent is selected from the group consisting of lower alkanols, glycols and polyglycols and mixtures thereof.

6. The process of claim 2 wherein said quaternizing agent consists of one or more compounds selected from the group consisting of methylchloride, dimethylsulfate, and diethylsulfate.

7. The process of claim 3 wherein said quaternizing agent consists of one or more compounds selected from the group consisting of methylchloride, methyl bromide, benzyl chloride, dimethylsulfate, and diethylsulfate.

* * * * *

UNITED STATES PATENT AND TRADEMARK OFFICE
CERTIFICATE OF CORRECTION

PATENT NO. : 5,491,240
DATED : February 13, 1996
INVENTOR(S) : Timothy C. Arnold, et al.

It is certified that error appears in the above-indentified patent and that said Letters Patent is hereby corrected as shown below:

Column 2, line 45: "TEE" should read --THE--

Column 2, line 59, Column 4, line 19 and Column 8, line 50:

" $\overline{CH_2-N=C(R^3)-N(R^2)CH_2}$ "

should read -- $\overline{CH_2-N=C(R^3)-N(R^2)CH_2}$ --

Column 3, line 30 & 49: " $\overline{CH_2-N=C(R^3)-N(Q)(R^2)CH_2}$ "

should read -- $\overline{CH_2-N=C(R^3)-N(Q)(R^2)CH_2}$ --

Signed and Sealed this

Twelfth Day of November, 1996

Attest:

BRUCE LEHMAN

Attesting Officer     Commissioner of Patents and Trademarks